(12) United States Patent
Singh et al.

(10) Patent No.: US 9,671,404 B2
(45) Date of Patent: Jun. 6, 2017

(54) USE OF MYELOID CELL BIOMARKERS FOR THE DIAGNOSIS OF CANCER

(75) Inventors: Harpreet Singh, Tuebingen (DE); Regina Mendrzyk, Freiburg im Breisgau (DE); Steffan Walter, Reutlingen (DE); Vincezq Bronte, Verona (IT); Susanna Mandruzzato, Padua (IT)

(73) Assignee: IMMATICS BIOTECHNOLOGIES GMBH, Munich (DE)

( * ) Notice: Subject to any disclaimer, the term of this patent is extended or adjusted under 35 U.S.C. 154(b) by 15 days.

(21) Appl. No.: 13/239,011

(22) Filed: Sep. 21, 2011

(65) Prior Publication Data

US 2012/0070461 A1   Mar. 22, 2012

Related U.S. Application Data

(60) Provisional application No. 61/384,784, filed on Sep. 21, 2010.

(30) Foreign Application Priority Data

Sep. 21, 2010 (GB) .................................. 1015765.9

(51) Int. Cl.
*G01N 33/574* (2006.01)
*G01N 33/50* (2006.01)

(52) U.S. Cl.
CPC ... *G01N 33/57419* (2013.01); *G01N 33/5047* (2013.01); *G01N 33/5743* (2013.01); *G01N 33/57438* (2013.01); *G01N 33/57446* (2013.01)

(58) Field of Classification Search
None
See application file for complete search history.

(56) References Cited

U.S. PATENT DOCUMENTS

| 2004/0136973 | A1* | 7/2004 | Huberman ........... C12N 5/0635 424/93.21 |
| 2007/0105142 | A1* | 5/2007 | Wilhelm ........................... 435/6 |
| 2009/0004213 | A1* | 1/2009 | Singh et al. ................ 424/185.1 |

OTHER PUBLICATIONS

Diaz-Montero et al. (Cancer Immunol. Immunother., 58:49-59, 2009).*
Gabrilovich et al. (Nature Reviews Immunology, 9:162-174, 2009).*
Mandruzzato et al. (J. Immunol., 182:6562-6568, 2009).*
Ostrand-Rosenberg et al. (Current Opinions in Genetics and Development, 18:11-18, 2008).*
Ko et al. (Clinical Cancer Research: 15(6):2148-2157, Mar. 2009).*
Umemura et al. (Journal of Leukocyte Biology, 83:1136-1144, 2008).*
Filipazzi et al., "Identification of a new subset of myeloid suppressor cells in peripheral blood of melanoma patients with modulation by a granulocyte-macrophage colony-stimulation factor-based antitumor vaccine", Journal of Clinical Oncology, Jun. 20, 2007, vol. 25, No. 18, pp. 2546-2553, American Society of Oral Oncology.
Kusmartsev et al., "Reversal of myeloid cell-mediated immunosuppression in patients with metastatic renal cell carcinoma", Clinical Cancer Research, Published online Dec. 15, 2008, vol. 14, No. 24, pp. 8270-8278, American Association for Cancer Research.
Mandruzzato et al., "IL4Ralpha+ myeloid-derived suppressor cell expansion in cancer patients", Journal of Immunology, May 15, 2009, vol. 182, pp. 6562-6568, The American Association of Immunologist, Inc.
Mirza et al., "All-trans-retinoic acid improves differentiation of myeloid cells and immune response in cancer patients" Cancer Research, Published online Sep. 15, 2006, vol. 66, No. 18, pp. 9299-9307, American Association for Cancer Research.
Schmielau et al., "Activated granulocytes and granulocyte-derived hydrogen peroxide are the underlying mechanism of suppression of t-cell function in advanced cancer patients", Cancer Research, Jun. 15, 2001, vol. 61, pp. 4756-4760, American Association for Cancer Research.
Zea et al., "Arginase-producing myeloid suppressor cells in renal cell carcinoma patients: a mechanism of tumor evasion", Cancer Research, Published online Apr. 15, 2005, vol. 65, No. 8, pp. 3044-3048, American Association for Cancer Research.

* cited by examiner

*Primary Examiner* — Misook Yu
*Assistant Examiner* — Nelson B Moseley, II
(74) *Attorney, Agent, or Firm* — McBee Moore Woodward & Vanik IP, LLC.

(57) ABSTRACT

The present invention relates to the use of myeloid cell biomarkers for the differential diagnosis, prognosis, and monitoring of renal cell carcinoma (RCC) or colorectal cancer (CRC). The present invention furthermore relates to monitoring the effect of a treatment against renal cell carcinoma (RCC) or colorectal cancer (CRC), and establishing a prognosis of the outcome of the treatment of renal cell carcinoma (RCC) or colorectal cancer (CRC). The present invention furthermore relates to panels of cellular biomarkers for use in the above methods, in particular multicolor panels for measuring said biomarkers.

5 Claims, 4 Drawing Sheets

SEQUENCE LISTING

```
<160> NUMBER OF SEQ ID NOS: 37

<210> SEQ ID NO 1
<211> LENGTH: 16
<212> TYPE: PRT
<213> ORGANISM: Homo sapiens

<400> SEQUENCE: 1

Ser Gln Asp Asp Ile Lys Gly Ile Gln Lys Leu Tyr Gly Lys Arg Ser
1               5                   10                  15

<210> SEQ ID NO 2
<211> LENGTH: 9
<212> TYPE: PRT
<213> ORGANISM: Homo sapiens

<400> SEQUENCE: 2
```

```
Val Met Ala Gly Asp Ile Tyr Ser Val
1               5
```

<210> SEQ ID NO 3
<211> LENGTH: 9
<212> TYPE: PRT
<213> ORGANISM: Homo sapiens

<400> SEQUENCE: 3

```
Ser Val Ala Ser Thr Ile Thr Gly Val
1               5
```

<210> SEQ ID NO 4
<211> LENGTH: 9
<212> TYPE: PRT
<213> ORGANISM: Homo sapiens

<400> SEQUENCE: 4

```
Ala Leu Ala Asp Gly Val Gln Lys Val
1               5
```

<210> SEQ ID NO 5
<211> LENGTH: 9
<212> TYPE: PRT
<213> ORGANISM: Homo sapiens

<400> SEQUENCE: 5

```
Leu Leu Gly Ala Thr Cys Met Phe Val
1               5
```

<210> SEQ ID NO 6
<211> LENGTH: 9
<212> TYPE: PRT
<213> ORGANISM: Homo sapiens

<400> SEQUENCE: 6

```
Ser Val Phe Ala Gly Val Val Gly Val
1               5
```

<210> SEQ ID NO 7
<211> LENGTH: 9
<212> TYPE: PRT
<213> ORGANISM: Homo sapiens

<400> SEQUENCE: 7

```
Ala Leu Phe Asp Gly Asp Pro His Leu
1               5
```

<210> SEQ ID NO 8
<211> LENGTH: 9
<212> TYPE: PRT
<213> ORGANISM: Homo sapiens

<400> SEQUENCE: 8

```
Tyr Val Asp Pro Val Ile Thr Ser Ile
1               5
```

<210> SEQ ID NO 9
<211> LENGTH: 9
<212> TYPE: PRT
<213> ORGANISM: Homo sapiens

<400> SEQUENCE: 9

```
Ser Thr Ala Pro Pro Val His Asn Val
1               5
```

<210> SEQ ID NO 10
<211> LENGTH: 9
<212> TYPE: PRT
<213> ORGANISM: Homo sapiens

<400> SEQUENCE: 10

Leu Ala Ala Leu Pro His Ser Cys Leu
1               5

<210> SEQ ID NO 11
<211> LENGTH: 9
<212> TYPE: PRT
<213> ORGANISM: Homo sapiens

<400> SEQUENCE: 11

Ala Leu Ser Asn Leu Glu Val Thr Leu
1               5

<210> SEQ ID NO 12
<211> LENGTH: 9
<212> TYPE: PRT
<213> ORGANISM: Homo sapiens

<400> SEQUENCE: 12

Ile Leu Ala Pro Val Ile Leu Tyr Ile
1               5

<210> SEQ ID NO 13
<211> LENGTH: 9
<212> TYPE: PRT
<213> ORGANISM: Homo sapiens

<400> SEQUENCE: 13

Ile Leu Asp Gln Lys Ile Asn Glu Val
1               5

<210> SEQ ID NO 14
<211> LENGTH: 10
<212> TYPE: PRT
<213> ORGANISM: Homo sapiens

<400> SEQUENCE: 14

Lys Leu Met Asp Leu Asp Val Glu Gln Leu
1               5                   10

<210> SEQ ID NO 15
<211> LENGTH: 10
<212> TYPE: PRT
<213> ORGANISM: Homo sapiens

<400> SEQUENCE: 15

Ala Leu Phe Val Arg Leu Leu Ala Leu Ala
1               5                   10

<210> SEQ ID NO 16
<211> LENGTH: 10
<212> TYPE: PRT
<213> ORGANISM: Homo sapiens

<400> SEQUENCE: 16

Lys Ile Phe Asp Glu Ile Leu Val Asn Ala
1               5                   10

```
<210> SEQ ID NO 17
<211> LENGTH: 15
<212> TYPE: PRT
<213> ORGANISM: Homo sapiens

<400> SEQUENCE: 17

Thr Pro Pro Ile Asp Ala His Thr Arg Asn Leu Leu Arg Asn His
1               5                   10                  15

<210> SEQ ID NO 18
<211> LENGTH: 16
<212> TYPE: PRT
<213> ORGANISM: Homo sapiens

<400> SEQUENCE: 18

Ser Pro Gln Tyr Ser Trp Arg Ile Asn Gly Ile Pro Gln Gln His Thr
1               5                   10                  15

<210> SEQ ID NO 19
<211> LENGTH: 9
<212> TYPE: PRT
<213> ORGANISM: Homo sapiens

<400> SEQUENCE: 19

Tyr Leu Ser Gly Ala Asn Leu Asn Leu
1               5

<210> SEQ ID NO 20
<211> LENGTH: 10
<212> TYPE: PRT
<213> ORGANISM: Homo sapiens

<400> SEQUENCE: 20

Leu Tyr Gln Ile Leu Gln Gly Ile Val Phe
1               5                   10

<210> SEQ ID NO 21
<211> LENGTH: 9
<212> TYPE: PRT
<213> ORGANISM: Homo sapiens

<400> SEQUENCE: 21

Ser Tyr Asn Pro Leu Trp Leu Arg Ile
1               5

<210> SEQ ID NO 22
<211> LENGTH: 9
<212> TYPE: PRT
<213> ORGANISM: Homo sapiens

<400> SEQUENCE: 22

Asn Tyr Leu Pro Phe Ile Met Glu Leu
1               5

<210> SEQ ID NO 23
<211> LENGTH: 9
<212> TYPE: PRT
<213> ORGANISM: Homo sapiens

<400> SEQUENCE: 23

Ser Tyr Ile Asp Val Leu Pro Glu Phe
1               5

<210> SEQ ID NO 24
<211> LENGTH: 9
```

<212> TYPE: PRT
<213> ORGANISM: Homo sapiens

<400> SEQUENCE: 24

Ser Tyr Ile Ile Asp Pro Leu Asn Leu
1               5

<210> SEQ ID NO 25
<211> LENGTH: 10
<212> TYPE: PRT
<213> ORGANISM: Homo sapiens

<400> SEQUENCE: 25

Tyr Tyr Asn Ala Ala Gly Phe Asn Lys Leu
1               5                   10

<210> SEQ ID NO 26
<211> LENGTH: 9
<212> TYPE: PRT
<213> ORGANISM: Homo sapiens

<400> SEQUENCE: 26

Asn Tyr Leu Leu Tyr Val Ser Asn Phe
1               5

<210> SEQ ID NO 27
<211> LENGTH: 9
<212> TYPE: PRT
<213> ORGANISM: Homo sapiens

<400> SEQUENCE: 27

Ala Tyr Leu Val Tyr Thr Asp Arg Leu
1               5

<210> SEQ ID NO 28
<211> LENGTH: 9
<212> TYPE: PRT
<213> ORGANISM: Homo sapiens

<400> SEQUENCE: 28

His Tyr Lys Pro Thr Pro Leu Tyr Phe
1               5

<210> SEQ ID NO 29
<211> LENGTH: 10
<212> TYPE: PRT
<213> ORGANISM: Homo sapiens

<400> SEQUENCE: 29

Val Trp Ser Asp Val Thr Pro Leu Thr Phe
1               5                   10

<210> SEQ ID NO 30
<211> LENGTH: 9
<212> TYPE: PRT
<213> ORGANISM: Homo sapiens

<400> SEQUENCE: 30

Thr Met Leu Ala Arg Leu Ala Ser Ala
1               5

<210> SEQ ID NO 31
<211> LENGTH: 9
<212> TYPE: PRT
<213> ORGANISM: Homo sapiens

<400> SEQUENCE: 31

Leu Thr Phe Gly Asp Val Val Ala Val
1               5

<210> SEQ ID NO 32
<211> LENGTH: 9
<212> TYPE: PRT
<213> ORGANISM: Homo sapiens

<400> SEQUENCE: 32

Asn Leu Asp Thr Leu Met Thr Tyr Val
1               5

<210> SEQ ID NO 33
<211> LENGTH: 9
<212> TYPE: PRT
<213> ORGANISM: Homo sapiens

<400> SEQUENCE: 33

Ala Met Thr Gln Leu Leu Ala Gly Val
1               5

<210> SEQ ID NO 34
<211> LENGTH: 9
<212> TYPE: PRT
<213> ORGANISM: Homo sapiens

<400> SEQUENCE: 34

Gly Leu Trp His His Gln Thr Glu Val
1               5

<210> SEQ ID NO 35
<211> LENGTH: 9
<212> TYPE: PRT
<213> ORGANISM: Homo sapiens

<400> SEQUENCE: 35

Lys Ile Gln Glu Ile Leu Thr Gln Val
1               5

<210> SEQ ID NO 36
<211> LENGTH: 9
<212> TYPE: PRT
<213> ORGANISM: Homo sapiens

<400> SEQUENCE: 36

Ala Leu Trp Ala Trp Pro Ser Glu Leu
1               5

<210> SEQ ID NO 37
<211> LENGTH: 17
<212> TYPE: PRT
<213> ORGANISM: Homo sapiens

<400> SEQUENCE: 37

Thr Phe Ser Tyr Val Asp Pro Val Ile Thr Ser Ile Ser Pro Lys Tyr
1               5                   10                  15

Gly

USE OF MYELOID CELL BIOMARKERS FOR THE DIAGNOSIS OF CANCER

CROSS REFERENCE TO RELATED APPLICATION

This application is a non provisional application which claims priority to U.S. Provisional Application No. 61/384,784, filed Sep. 21, 2010, and U.K. Application GB 1015765.9, filed on Sep. 21, 2010, each of which is incorporated by reference in its entirety.

BACKGROUND

A. Field of the Invention

The present invention relates to the use of myeloid cell biomarkers for the differential diagnosis, prognosis, and monitoring of renal cell carcinoma (RCC) or colorectal cancer (CRC). The present invention furthermore relates to monitoring the effect of a treatment against renal cell carcinoma (RCC) or colorectal cancer (CRC), and establishing a prognosis of the outcome of the treatment of renal cell carcinoma (RCC) or colorectal cancer (CRC). The present invention furthermore relates to panels of cellular biomarkers for use in the above methods, in particular multicolor panels for measuring said biomarkers.

For the purposes of the present invention, all references as cited herein are incorporated by reference in their entireties.

B. Brief Description of Related Art

In Europe, renal cell carcinoma (RCC) ranks as the seventh most common malignancy in men, amongst whom there are 29,600 new cases each year (3.5% of all cancers). Among women, there are 16,700 cases a year (ranks twelfth or 2.3% of all cancers). RCC is rare before the age of 40, and above this age it is twice as common in men as in women. Incidence by age rises rapidly from less than 2 per 100,000/year in patients under 40 years old to 38 per 100,000/year in the age group 65-69 years, thereafter it increases to 46 per 100,000/year in those older than 75 years.

A total of 25-30% of patients with RCC displays overt metastases at initial presentation. About one third of patients with kidney cancer will develop metastatic disease over time. Thus, nearly 50-60% of all patients with RCC will eventually present with metastatic disease. Among those with metastatic disease, approximately 75% have lung metastases, 36% lymph node and/or soft tissue involvement, 20% bone involvement, and 18% liver involvement.

RCC is the most lethal carcinoma of the genitourinary tumors with a 65% five-year survival rate compared to the 82% and 100% five-year survival rate for bladder or prostate cancer respectively (US 1972-2001 data). European average survival rates at 5 years (up to 1999) after diagnosis (1990-1994) for kidney cancer were about 58%, and RCC was classified by several authors as a cancer with only moderate prognosis. Overall, RCC is fatal in nearly 80% of patients. This figure indicates a strong medical need for effective and early clinical follow-up and treatment for recurrences.

The American Joint Committee on Cancer (MCC) has established staging of RCC by TNM classification (Kidney. In: American Joint Committee on Cancer 2002, TNM Classification of renal cell carcinoma). The staging system for renal cell cancer is based on the degree of tumor spread beyond the kidney.

Survival strongly depends on the stage at which the tumor is diagnosed: 5-year survival is only 12% for patients bearing lesions with distant metastases, but 80% for those with localized malignancies.

Globally, colorectal carcinoma (CRC) is the third most common cancer. Colon and rectum cancer account for about 1 million new cases per year, and unlike as for most other tumors, numbers are not so different in men and women (ratio, 1.2:1). In Europe, CRC is the second most common cancer and the second most common cancer-related cause of death in both men and women with approx. 380,000 new cases and about 200,000 disease-related deaths per year. The raw incidence rate in 2002 for men and women was 88.3 and 84.0/100,000, respectively; the raw mortality was 34.8 and 35.2/100,000, respectively. These data clearly reflect the significance of CRC as an enormous source of both individual and societal burden. CRC is a cancer of the elderly population as the mean age at the time of disease manifestation in men and women is 69 and 75 years, respectively. Besides dietary and lifestyle factors (e.g. obesity, lack of physical exercise, smoking, regular alcohol consumption) other risk factors are familial occurrence of CRC, hereditary CRCs (familial adenomatous polyposis [FAP], attenuated FAP [attenuated adenomatous polyposis coli; AAPC], hereditary non-polyposis colorectal carcinoma [HNPCC], hamartomatous polyposis syndromes) and inflammatory bowel diseases such as ulcerative colitis or Crohn's disease.

CRC mostly occurs as adenocarcinoma of the mucous membranes in rectum, sigma, colon transversum/descendens, and colon ascendens/caecum. Early colorectal carcinoma may be cured by primary surgery. Distant metastases, however, spread to regional lymph nodes and to liver, lung, and other organs (such as CNS). Due to unspecific symptoms, CRC will often be diagnosed at a relatively late stage and approx. 25% of patients with CRC will have metastatic disease (mCRC) when first presented to their physicians. An additional 30% of newly diagnosed patients with localized resectable CRC will subsequently develop a metastatic recurrence.

Besides the Dukes' system, CRC is usually staged using the TNM system developed by the AJCC (latest revision in 2002), which compartmentalizes carcinomas according to the depth of invasion of the primary tumor, the absence or presence of regional lymph node metastases, and the absence or presence of distant metastases. As the possible number of resulting categories is very large, various categories are therefore grouped under Stages I through IV. Recently, Stage III was further subdivided into Stages IIIA to IIIC, since these were identified as significant independent prognostic covariates.

During the past three decades, cancer-related mortality has shown a continuous decrease. Meanwhile, the overall 5-year survival rate in men and women has increased to 63%. This survival increase may largely be attributed to improvements in surgical management, adjuvant therapy for localized high-risk disease, and the multimodality management of advanced metastatic disease.

Myeloid derived suppressor cells (MDSCs) is a term describing several cellular subsets of myeloid cells with immunosuppressive properties that have been discussed to be relevant in the biology of cancer immune editing.

Myeloid-derived suppressor cells (MDSC) contribute to immune dysfunctions induced by tumors both in experimental models and patients. In tumor-bearing mice, MDSC are phenotypically heterogeneous cells that vary in their surface markers, likely depending on soluble factors produced by different tumors at different stages of maturation, as well as in cancer patients that very efficiently suppress T cell function. It is known that a growing tumor stimulates myelopoiesis and affects cell differentiation through the production of growth factors and cytokines.

Lechner et al. (in: Lechner M G, Liebertz D J, Epstein A L. Characterization of cytokine-induced myeloid-derived suppressor cells from normal human peripheral blood mononuclear cells. J. Immunol. 2010 Aug. 15; 185(4):2273-84. Epub 2010 Jul. 19) describe that in cancer patients, increased MDSCs correlate with more aggressive disease and a poor prognosis. Expression of 15 immune factors (TGFbeta, IL-1beta, IL-4, IL-6, IL-10, GM-CSF, M-CSF, IDO, fms-related tyrosine kinase 3 ligand, c-kit ligand, inducible NO synthase, arginase-1. TNF-alpha, cyclo-oxygenase 2, vascular endothelial growth factor [VEGF]) by MDSC-inducing human solid tumor cell lines were evaluated by RT-PCR. Based upon these data, cytokine mixtures were then tested for their ability to generate suppressive CD33(+) cells from healthy donor PBMCs in vitro by measuring their ability to inhibit the proliferation of, and IFN-gamma production by, fresh autologous human T cells after CD3/CD28 stimulation. The authors suggest that some cytokines are potential therapeutic targets for the inhibition of MDSC induction in cancer patients.

Allan (in Nature Reviews Immunology 8, 828, November 2008) describes that Myeloid-derived suppressor cells (MDSCs) are a heterogeneous population of immune cells that accumulates in tumour-bearing hosts and in response to inflammation. Although it has been established that the capacity of MDSCs to inhibit T-cell responses prevents tumour rejection, the mechanisms that underlie MDSC accumulation and suppressor function are unclear.

Despite the above recent progresses in the diagnosis and management of RCC and CRC, still biological markers are needed that can be used to achieve an improved diagnosis, in particular a differential diagnosis, a prognosis, a monitoring of the effect, and an understanding of the best course of treatment of renal cell carcinoma (RCC) and/or colorectal cancer (CRC), in order to further improve the survival and to better adjust the treatment of people in need. Furthermore, the markers should also allow for a prognosis of the outcome of said treatment of renal cell carcinoma (RCC) or colorectal cancer (CRC). It is therefore an object of the present invention, to provide respective biological markers and diagnostic, prognostic and predictive methods.

SUMMARY OF THE INVENTION

In an aspect, said object is solved by providing a method for diagnosing and/or prognosing cancer, comprising determining the level of at least one myeloid-derived suppressor cell (MDSC) phenotype in an MDSC population in a sample comprising peripheral blood mononuclear cells (PBMC) obtained from a patient based on at least one MDSC phenotype marker, wherein said marker is selected from the group consisting of CD15; IL4Ra; CD14; CD11b; HLA-DR; CD33; Lin; FSC; SSC; and, optionally CD45; CD18; CD80; CD83; CD86; HLA-I; a Live/Dead discriminator and wherein an increase of the level of said MDSC phenotypes compared to a non-cancer patient sample is indicative for cancer and/or a prognostic indicator for a treatment of said cancer.

DETAILED DESCRIPTION OF THE INVENTION

Figure 1:
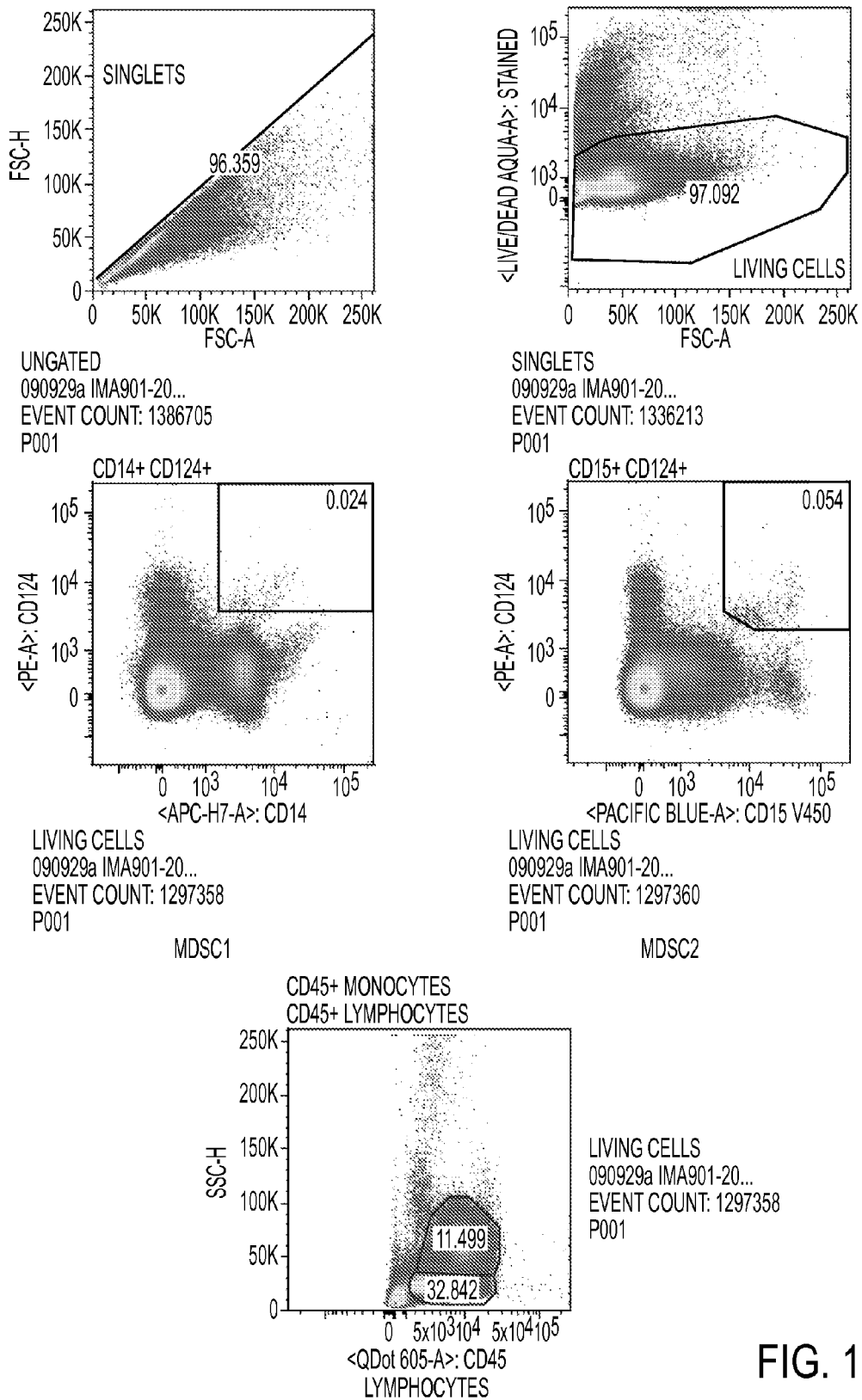
FIG. 1 shows an exemplary MDSC staining with the respective gating strategy. Identical gates were used for all samples. MDSC1-2 and lymphocytes were gated as subpopulations from singlets and living lymphocytes while MDSC3-6 were gated as subpopulations from singlets.
Figure 1:
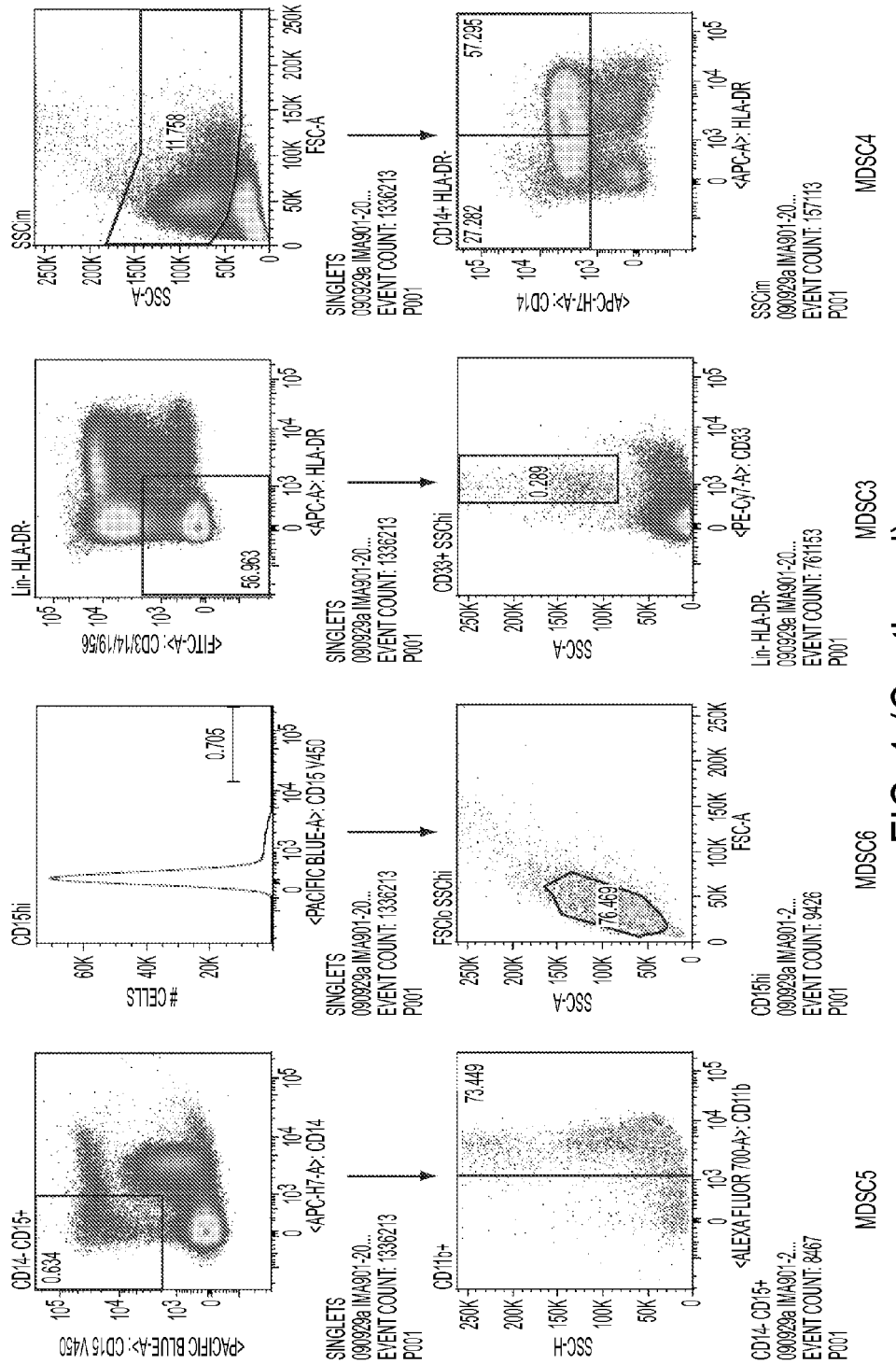

In a first aspect of the present invention, said object is solved by providing a method for diagnosing and/or prognosing cancer, comprising determining the level of at least one myeloid-derived suppressor cell (MDSC) phenotype in an MDSC population in a sample comprising peripheral blood mononuclear cells (PBMC) obtained from a patient based on at least one MDSC phenotype marker, wherein said marker is selected from the group consisting of CD15; IL4Ra; CD14; CD11b; HLA-DR; CD33; Lin; FSC; SSC; and, optionally CD45; CD18; CD80; CD83; CD86; HLA-I; a Live/Dead discriminator and wherein an increase of the level of said MDSC phenotypes compared to a non-cancer patient sample is indicative for cancer and/or a prognostic indicator for a treatment of said cancer.

All the markers as described above are known in the state of the art. Regarding Live/Dead discriminators, live cells have intact membranes and are impermeable to dyes such as propidium iodide (PI), which only leaks into cells with compromised membranes. Thiazole orange* (TO) is a permeant dye and enters all cells, live and dead, to varying degrees. With gram-negative organisms, depletion of the lipopolysaccharide layer with EDTA greatly facilitates TO uptake. Thus a combination of these two dyes provides a rapid and reliable method for discriminating live and dead cells. If enumeration of the bacteria is important, BD Liquid Counting Beads (BD Biosciences, San Jose, Calif.), a flow-cytometry bead standard, can be used to accurately quantify the number of live, dead, and total bacteria in a sample. Other Live/Dead discriminators are described herein or know in the state of the art, and are described in, for example, Perfetto et al. (Perfetto S P, Chattopadhyay P K, Lamoreaux L, Nguyen R, Ambrozak D, Koup R A, Roederer M. Amine reactive dyes: an effective tool to discriminate live and dead cells in polychromatic flow cytometry. J Immunol Methods. 2006 Jun. 30; 313(1-2):199-208. Epub 2006 May 19.)

In Peranzoni, et al., "Myeloid-derived suppressor cell heterogeneity and subset definition", Current Opinion in Immunology, Vol. 22, No. 2, epub February 2010, pages 238-244, a CD15+/CD11B+/CD14− population is mentioned to be observed in renal cell cancer patients. Absence in healthy donors is mentioned for a different population (CD14+CD11b+HLA-Drlo/neg). Furthermore, a monitoring in vaccine programme is shown for a different population (CD11b+CD33+CD15+). A significant increase in patients plus Trend from stage I to IV is shown for a different population (Lin-HLA-DR-CD33+CD11b+). S. Kusmartsev, et al., "Expansion of CD11b(+)CD33(low)CD15(high) immunosuppressive myeloid cell population in patients with bladder carcinoma", Proceedings of the American Association for Cancer Research Annual Meeting, Vol. 51, April 2010, pages 1291-1292 discloses the presence of a different population (CD11b+CD15hi CD33lo) elevated in cancer compared to healthy donors. In addition to that, only in vitro contribution to immune suppression is shown. In WO 2010/055340 A1, the population CD11+CD15+ is reportedly increased in cancer patients as compared to healthy donors. In Ko et al., "Sunitinib mediates reversal of myeloid-derived suppressor cell accumulation in renal cell carcinoma patients.", Clinical Cancer Research, Vol. 15, No. 6, March 2009, page 2148-2157, two MDSC populations (CD14– CD15+ and CD33+HLA-DR–) were shown to be increased as compared to healthy control donors. All these publications may only generally imply a diagnostic value but no prognostic or predictive value of MDSC populations.

Liu Chien-Ying, et al., "Population alterations of l-arginase- and inducible nitric oxide synthaseexpressed CD11b (+)/CD14(–)/CD15(+)/CD33(+) myeloid-derived suppressor cells and CD8(+) T lymphocytes in patients with advanced-stage non-small cell lung cancer", Journal of Cancer Research and Clinical Oncology, Vol. 136, No. 1, January 2010, pages 35-45 discloses that CD11b+/CD14– MDSC levels of NSCLC patients were increased in patients versus healthy control subjects. CD11b+/CD14– MDSC levels of NSCLC patients were lower if the patients had benefited from previous chemotherapy (PR+SD vs. PD: FIG. 5A). However, this analysis was done after the clinical progression and hence no prognostic value can be inferred. Furthermore, the expression of CD15+ and CD33+ on this cell population was not used for the analysis.

Figure 2:
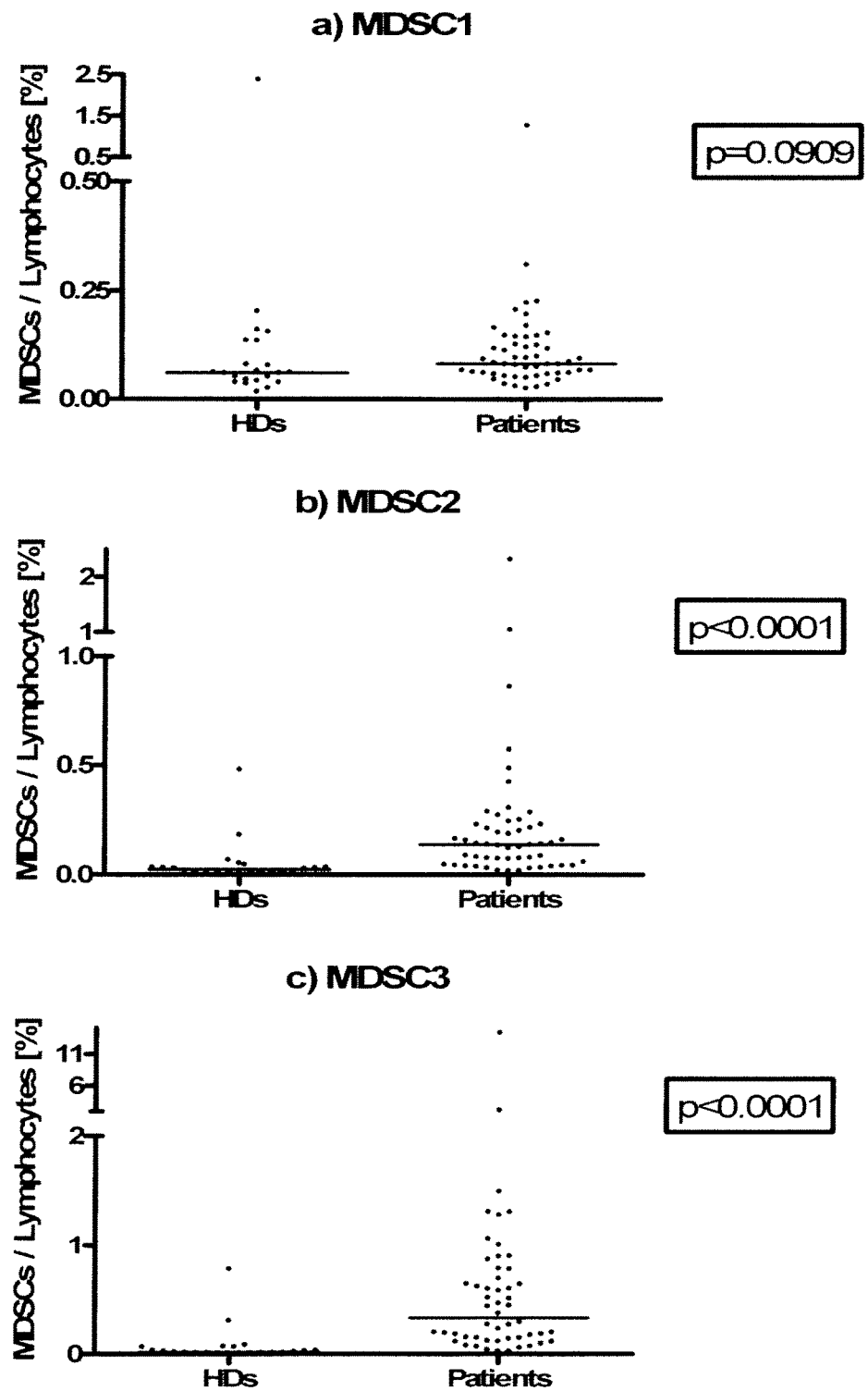
FIGS. 2a) to 2f) show the comparison of IMA901-202 patients and age-matched healthy donors. Shown are pre-treatment MDSC levels of individual patients of the ITT populations that were MDSC evaluable and age <70 years (N=52) and of healthy donors (N=22). Bars denote medians, p-values have been calculated by Mann-Whitney test, 2-sided.
Figure 2:
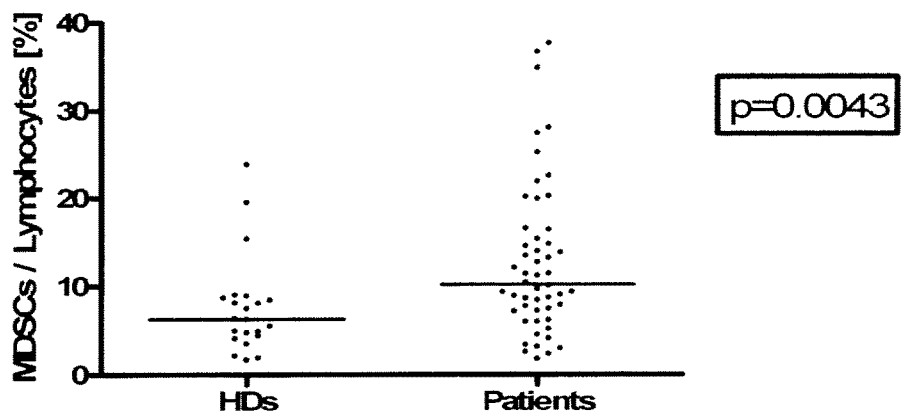
Figure 2:
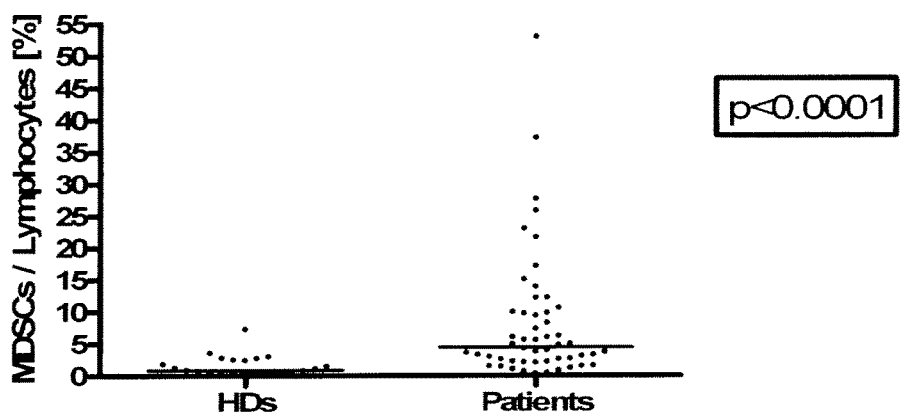
Figure 2:
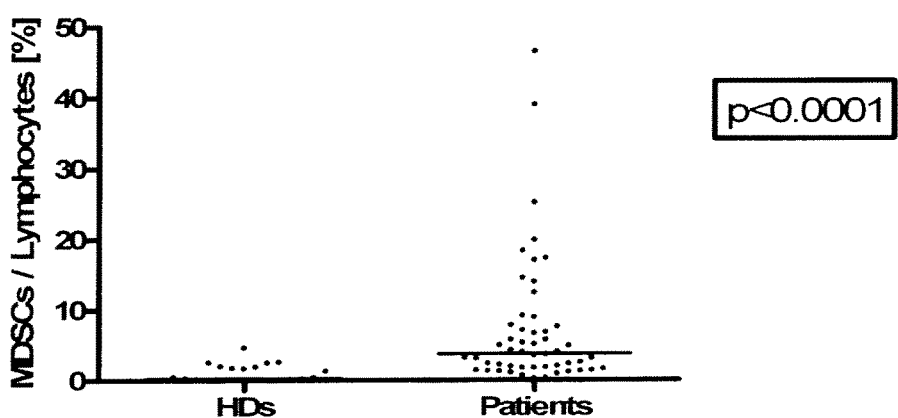

In M Diaz-Montero, et al., "Increased circulating myeloid-derived suppressor cells correlate with clinical cancer stage, metastatic tumor burden, and doxorubicin-cyclophosphamide chemotherapy", Cancer Immunology Immunotherapy, Vol. 58, No. 1, January 2009, pages 49-59, it is shown that MDSC levels in newly diagnosed (various) cancer patients were increased as compared to healthy donors (FIG. 2A). High MDSC levels were correlated with higher tumor stage (FIG. 2B-C). Within stage IV patients, patients with higher tumor burden had higher MDSC levels (FIG. 3). FIG. 5 indicates that MDSC levels are influenced by different types of chemotherapy. However, no predictive value of response to therapy can be inferred from that data.

In S Mandruzzato, et al., "IL4R alpha(+) Myeloid-Derived Suppressor Cell Expansion in Cancer Patients", Journal of Immunology, Vol. 182, No. 10, May 2009, pages 6562-6568 the following populations are shown to be increased in PBMCs of patients vs healthy donors; CD14+ (FIG. 5A), CD15+ (FIG. 5B), IL4Ra+/CD14+ (FIG. 2A). Association with tumor is shown for CD14+ cells in colon cancer and melanoma tissue (FIG. 5C-D). These data only generally implies a diagnostic value but no prognostic or predictive value of MDSC populations.

Finally, S Kusmartsev, et al., "Reversal of myeloid cell-mediated immunosuppression in patients with metastatic renal cell carcinoma", Clinical Cancer Research, Vol. 14, No. 24, December 2008, pages 8270-8278, shows that a population of Lin-HLA-DR-cells is increased in the PBMCs of RCC patients vs. healthy donors (FIG. 1B). The document further shows the expression of CD33+ on one Lin-HLA-DR-sample. These data also only generally implies a diagnostic value but no prognostic or predictive value of MDSC populations.

Generally, the present invention is not limited to a particular cancer or cancer stage. Nevertheless, preferred is a method according to the present invention, wherein said cancer is a cancer which can be treated by immunotherapy, and is preferably selected from renal cell carcinoma (RCC), colorectal cancer (CRC), gastric cancer (GC), melanoma, and adenocarcinoma.

The samples as analyzed in the context of the present invention can be any biological sample which contains MDSCs as obtained from a subject (such as a patient or non-cancer patient or healthy individual). Preferably, said sample is a blood sample, such as whole blood, frozen whole blood, peripheral blood, or fractions thereof, preferably buffy coat comprising peripheral blood mononuclear cells (PBMC). Also, RNA can be obtained from any of these samples. Furthermore, myeloid cells can also be isolated from tumor tissue or bone marrow.

The invention is based on the surprising finding that pre-treatment levels of MDSCs are a relevant biomarker for immune and/or other clinical responses in cancer treatment patients, such as, for example, immunotherapy patients treated with an anticancer vaccine, such as IMA901-202 (described, for example, at the Annual Meeting of the American Society of Clinical Oncology (ASCO) in Chicago, USA, Jun. 2 to Jun. 5, 2007) or other IMA-vaccines as described herein. The invention further discloses that in cancer patients, and in particular RCC patients, the pre-treatment MDSC levels differ between healthy donors and among different subgroups of RCC patients (all patients, +Cy, –Cy, prior therapies cytokines, TKIs, sorafenib, sunitinib). The invention thus relates to diagnostic, prognostic and predictive marker for cancer, in particular RCC and CRC, as well as a multicolor panel for measuring said biomarkers.

Myeloid cells are derived from myeloid stem cells and include erythrocytes, thrombocytes, neutrophils, monocytes and macrophages, eosinophils, basophils, and mast cells. In the context of the present invention, after PBMC analysis six phenotypes of human MDSCs (MDSC1-6) were identified and defined, as shown in table 1.

TABLE 1

Human MDSC phenotypes found in PBMCs and reported in primary publications

| Population | Reference | Phenotype | Sample type | Patient population (according to literature) |
|---|---|---|---|---|
| MDSC1 | (Mandruzzato et al., 2009) | CD14+ IL4Ra+ | PBMCs | RCC and CRC |
| MDSC2 | (Mandruzzato et al., 2009) | CD15+ IL4Ra+ | PBMCs | RCC and CRC |
| MDSC3 | (Kusmartsev et al., 2008; Mirza et al., 2006) | Lin– HLA– DR– CD33+ (CD18+ HLAI+) | PBMCs | Healthy donors, stage III-IV RCC patients |
| MDSC4 | (Filipazzi et al., 2007) | CD14+ HLA– DR(–/lo) FSChi SSCim | PBMCs | Healthy donors, stage IV melanoma patients |
| MDSC5 | (Zea et al., 2005) | CD11b+ CD14– CD15+ (FSChi SSCim CD80– CD83– CD86– HLA– DR–) | PBMCs | Healthy donors, metastatic RCC patients |
| MDSC6 | (Schmielau and Finn, 2001) | CD15+ FSClo SSChi | PBMCs | Healthy donors, metastatic adenocarcinoma patients |

In the context of the present invention, an MDSC-phenotype marker panel (or set) was established in order to provide for a quick and effective identification and characterization of the MDSC-phenotypes in diagnostics. For this, the most informative markers for the different phenotypes were selected as shown in the following table 2.

TABLE 2

Selection of human MDSC markers with decreasing priority (markers in brackets are optional)

| Marker | Function and cellular expression pattern in blood | PFC Category[#] | Priorisation (number of measurable phenotypes, if in panel) |
|---|---|---|---|
| CD15 | CH moiety (3-fucosyl-N-acetyllactosamin) and adhesion molecule. Highly expressed on neutrophil and eosinophil granulocytes. Partially expressed on monocytes. Not expressed on lymphocytes or basophils. | 1° | 1/6 |
| IL4Ra = CD124 | Alpha subunit of the IL4R complex. Different forms of the IL4R can bind to IL-4 and/or IL-13. Expressed on a variety of hematopoietic cells. | 3° | 2/6 |
| CD14 | High affinity receptor for LPS. Highly expressed on monocytes. | 1° | 3/6 |
| CD11b | Part of CD11b:CD18 complex. Adhesion molecule and complement receptor. Binds to ICAM1-3. Expressed on monocytes, granulocytes, NK cells and activated lymphocytes. | 2° | 4/6 |
| HLA-DR | Class II MHC. Expressed on B cells, T cells, activated T cells, APCs. | 2° | 5/6 |
| CD33 | Unknown function, usually considered myeloid-specific. Expressed on immature myeloid cells, mature monocytes, activated T cells. Not expressed on platelets, lymphocytes, erythrocytes. | 3° | 5/6 |
| Lin | Combination of CD3, CD14, CD19, CD56; => Lineage marker for conventional lineages among PBMCs (T-cells, B-cells, Monocytes, NK cells) | 2° | 6/6 |
| (L/D) | Dead cells (loss of membrane integrity) | — | — |
| (CD45) | Leukocyte common antigen expressed on all leukocytes. Absent from erythrocytes and thrombocytes. | 1° | — |

[#]Polychromatic flow cytometry category analogous to (Mahnke and Roederer, 2007)

Preferred is therefore a method according to the present invention, wherein said MDSC phenotype is selected from
a) MDSC1, which can be identified based on the markers IL4Ra+ and CD14+;
b) MDSC2, which can be identified based on markers IL4Ra+ and CD15+;
c) the group of MDSC1 or 2 which can be identified and/or distinguished from the other MDSCs 2 to 6 or 1, and 3 to 6, respectively, based on marker IL4Ra+;
d) MDSC3, which can be identified based on markers Lin-, HLA-DR-, and CD33+, optionally together with CD18+ and HLAI+;
e) MDSC4, which can be identified based on markers CD14+; HLA-DR(-/lo); FSChi; and SSCim;
f) MDSC5, which can be identified based on markers CD11b+; CD14-; and CD15+; optionally together with FSChi; SSCim; CD80-; CD83-; CD86-; and HLA-DR-; and
g) MDSC6 based on CD15+; FSClo; and SSChi.

In the context of the present invention, identifying shall mean the identification of the MDSC-phenotype, or distinguishing between the six MDSC-phenotypes.

The person of skill will further be aware that, based on the markers as presented herein, efficient marker panels can be generated in cases where only one or two or more but less than all six of the MDSC phenotypes as described herein shall be selectively identified. A preferred example is the MDSC5-phenotype, the individual identification of which is useful for a prognostic diagnosis regarding outcome (see table 3) and/or in cyclophosphamide pre-treated patients, as described below.

The cellular markers as described herein can be identified in accordance with methods of the state of the art. Preferred examples are Epigenomics (i.e. methylation analysis in the genes of the markers as described herein, preferably their introns, exons, introns/exon borders, promoters, and 5'- or 3'-located UTRs), transcriptomics or proteomics. Further preferred is immunostaining, i.e. an antibody-based method to detect a specific marker in a sample. Examples for immunostaining are flow cytometry, Western blotting, enzyme-linked immunosorbent assay (ELISA), and immuno-electron microscopy, preferred is flow cytometry. Further preferred is a method according to the present invention, wherein said method comprises flow cytometry comprising a single multicolor staining step. "Multicolor" refers to the use of different dyes (particularly fluorescent dyes) as described below.

In another important aspect of the present invention, the method according to the invention further comprises a prognosis, wherein an increased level of said MDSC phenotypes compared to pre-treatment MDSC levels in a sample is associated with shorter overall survival, tumor growth or progression-free survival, preferred is overall survival. Table 3 shows the correlation of pre-treatment MDSC levels and overall survival in the study group underlying the present invention.

TABLE 3

Correlation of pre-treatment MDSC levels and overall survival (study arm subgroups)

| | All (N = 57) | | +Cy (N = 26) | | −Cy (N = 31) | |
|---|---|---|---|---|---|---|
| | HR estimate | p | HR estimate | p | HR estimate | p |
| MDSC1 | 6,9617 | 0,6307 | 3743, 4765 | 0,1766 | 0,0527 | 0,6061 |
| MDSC2 | 2,0059 | 0,5076 | 1,1694 | 0,9640 | 1,4980 | 0,7150 |
| MDSC3 | 2,0681 | 0,1133 | 2,8586 | 0,1841 | 1.7469 | 0,3629 |
| MDSC4 | 1,0693 | *0,0332* | 1,0885 | 0,0987 | 1,0463 | 0,2539 |
| MDSC5 | 1,0965 | *0,0053* | 1,1499 | 0,0837 | 1,0745 | *0,0499* |
| MDSC6 | 1,0703 | 0,0687 | 0,9703 | 0,7992 | 1,0621 | 0,1057 |

Shown are hazard ratio (HR) estimates (cox proportional hazard model, estimated hazard ratio) and p values (likelihood ratio test) for analysis of pre-treatment MDSC levels as % per lymphocytes versus overall survival in the per protocol population that is evaluable for MDSC levels. Bold numbers indicate trends (p<0.15) or significant correlations (p<0.05) if italic.

Hazard Ratio>1 (underlined): Time to event shorter for patients with higher values. Cy=cyclophosphamide pre-treatment.

Further preferred is a (preferably prognostic) method according to the present invention, wherein said MDSC phenotype is selected from MDSC2, 3, 4, 5, and 6. It was found that—while levels of MDSC1 were not significantly different between patients and healthy donors—levels of MDSC2, 3, 4, 5, and 6 were highly significantly increased in patients as compared to healthy donors, as can be taken from FIG. 2, where a comparison of IMA901-202 patients (depicted by the dots) and age-matched healthy donors is shown based on pre-treatment MDSC levels of individual patients of the ITT populations that were MDSC evaluable and age <70 years (N=52) and of healthy donors (N=22). Bars denote medians, p-values have been calculated by Mann-Whitney test, 2-sided.

Based on the literature as cited herein, several of the MDSC phenotypes as described herein have been identified in certain cancer patient groups, showing the broad applicability of the present invention in cancers and the diagnosis and treatment thereof, particularly in renal cell carcinoma (RCC), colorectal cancer (CRC), gastric cancer (GC), melanoma, and adenocarcinoma. Therefore, preferred is a method according to the present invention, wherein said MDSC phenotype is selected from MDSC1 and/or 2 in an RCC or CRC patient; selected from MDSC3 in a stage III-IV RCC patients, selected from MDSC4 in a stage IV melanoma patient; selected from MDSC5 in a metastatic RCC patient; and selected from MDSC5 in a metastatic adenocarcinoma patient.

In another important aspect of the present invention, the method according to the invention relates to a method for detecting the effect of a cancer treatment in a patient, comprising determining the level of at least one myeloid-derived suppressor cell (MDSC) phenotype according to a method according to the invention in a biological sample obtained from a patient being treated for cancer, wherein a decrease of the level of said MDSC phenotype(s) is indicative for an effective treatment of said cancer in said patient. Said decrease can be detected in comparison to a control group, which is selected in accordance with the actual diagnostic scenario. One example is a control in view of a non-cancer patient, nevertheless, comparisons can also be made to other cancers and/or different genetic backgrounds in or between the patient group(s).

This aspect of the present invention is based on the effect of a suitable cancer treatment on the level of at least one myeloid-derived suppressor cell (MDSC) phenotype as found in the patient. In general, a decreased level of said MDSC phenotype(s) is indicative for an effective treatment of said cancer in said patient. Optimally, the decrease of the levels (amount and/or proportion of the at least one myeloid-derived suppressor cell (MDSC) phenotype) of several MDSC phenotype(s) will indicate an efficient cancer treatment. Treatment includes both preventive and acute treatment, which can be evaluated through a remission of the cancerous disease that is treated. The cancer treatment can be selected from any treatment suitable for the respective cancer, and is, for example, selected from chemotherapy with an anti-cancer agent, and/or selected from cytokines, sorafenib, sunitinib, cyclophosphamide, and tyrosine kinase inhibitors (TKI) and/or immunotherapy, preferably comprising the use of an anti-cancer vaccine, for example as described herein, optionally together with GM-CSF.

In another aspect of the present invention, the method according to the present invention further comprises a monitoring of the effect of said cancer treatment in said patient, comprising repeating said determining step at least once. Usually, a monitoring is performed in regular intervals during the treatment, such as weekly, twice weekly, or even monthly.

Another important aspect of the present invention relates to a method according to the present invention, wherein said patient at the time of performing said method has been pre-treated with an anti-cancer agent selected from cytokines, sorafenib, sunitinib, cyclophosphamide, and tyrosine kinase inhibitors (TKI). In this case, in a preferred embodiment thereof, the method according to the present invention further comprises a prognosis of the effect of a cancer treatment in a patient, wherein said patient has been pre-treated with cyclophosphamide, and wherein a decrease of levels of the MDSC5 phenotype compared to a non-treated or pretreated patient sample is indicative for an effective treatment of said cancer in said patient. In this aspect, said cancer treatment can be selected from chemotherapy as described above, preferred is an immunotherapy, preferably comprising the use of an anti-cancer vaccine, optionally together with GM-CSF.

In the context of the present invention, the cancer treatment preferably is an immunotherapy, comprising the use of an anti-cancer vaccine. Immunotherapy and respective vaccines are described in the state of the art; immunotherapy in cancer patients aims at activating cells of the immune system specifically, especially the so-called cytotoxic T-cells (CTL, also known as "killer cells", also known as CD8-positive T-cells), against tumor cells but not against healthy tissue. Tumor cells differ from healthy cells by the expression of tumor-associated proteins. HLA molecules on the cell surface present the cellular content to the outside, thus enabling a cytotoxic T cell to differentiate between a healthy and a tumor cell. This is realized by breaking down all proteins inside the cell into short peptides, which are then attached to HLA molecules and presented on the cell surface (Rammensee et al., 1993). Peptides that are presented on tumor cells, but not or to a far lesser extent on healthy cells of the body, are called tumor-associated peptides (TUMAPs). The antigens that are recognized by the tumor specific T-lymphocytes, that is, their epitopes, can be molecules derived from all protein classes, such as enzymes, receptors, transcription factors, etc.

However, priming of one kind of CTL is usually insufficient to eliminate all tumor cells. Tumors are very mutagenic and thus able to respond rapidly to CTL attacks by changing their protein pattern to evade recognition by CTLs. To counter-attack the tumor evasion mechanisms a variety of specific peptides is used for vaccination. In this way a broad simultaneous attack can be mounted against the tumor by several CTL clones simultaneously. This may decrease the chances of the tumor to evade the immune response. This hypothesis has been recently confirmed in a clinical study treating late-stage melanoma patients. With only few exceptions, patients that had at least three distinct T-cell responses, showed objective clinical responses or stable disease (Banchereau et al., 2001) as well as increased survival (personal communication with J. Banchereau), while the vast majority of patients with less than three T-cell responses were diagnosed with progressive disease.

The preferred medicament as used in the context of the methods of the present invention is a tumor vaccine. Other preferred medicaments include DNA- or RNA-based vaccines, for example as described by Weide et al. (Weide B, Garbe C, Rammensee H G, Pascolo S. Plasmid DNA- and messenger RNA-based anti-cancer vaccination. Immunol Lett. 2008 Jan. 15; 115(1):33-42. Epub 2007 Oct. 26). The medicament may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. The peptides may be substantially pure, or combined with an immune-stimulating adjuvant (see below) or used in combination with immune-stimulatory cytokines, or be administered with a suitable delivery system, for example liposomes. The peptides may also be conjugated to a suitable carrier such as keyhole limpet haemocyanin (KLH) or mannan (see WO 95/18145 and Longenecker et al (1993)). The peptide may also be tagged, may be a fusion protein, or may be a hybrid molecule. The peptides whose sequence is given in the present invention are expected to stimulate CD4 or CD8 T cells. However, stimulation of CD8 CTLs is more efficient in the presence of help provided by CD4 T-helper cells. Thus, for MHC Class I epitopes that stimulate CD8 CTL the fusion partner or sections of a hybrid molecule suitably provide epitopes which stimulate CD4-positive T cells. Thus, the fusion partner or sections of a hybrid molecule suitably provide epitopes that stimulate CD4+ T-cells. CD4+ stimulating epitopes are well known in the art and include those identified in tetanus toxoid. In a further preferred embodiment the peptide is a fusion protein, in particular comprising N-terminal amino acids of the HLA-DR antigen-associated invariant chain (Ii). In one embodiment the peptide of the invention is a truncated human protein or a fusion protein of a protein fragment and another polypeptide portion provided that the human portion includes one or more amino acid sequences of the present invention.

For use, the vaccine may also include one or more adjuvants. Preferred adjuvants are imiquimod, resiquimod, GM-CSF, cyclophosphamide, sunitinib, bevacizumab, interferon-alpha, CpG oligonucleotides and derivates, poly-(1:C) and derivates, RNA, sildenafil, and particulate formulations with PLG or virosomes. As mentioned, the medicament is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients, 3. Ed. 2000, American Pharmaceutical Association and pharmaceutical press. The composition can be used for a prevention, prophylaxis and/or therapy of cancerous diseases, such as, for example, RCC and CRC. Exemplary peptide combinations for vaccines to be used in the context of the present invention are listed in the following tables 4A to 4D, and are herein designated as IMA901, IMA910, IMA941, and IMA950, respectively.

TABLE 4A

IMA901 (e.g. used in renal cancer)

| SEQ ID No: | Abbrev. | Protein | Sequence |
| --- | --- | --- | --- |
| 1 | MMP-001 | Matrix metalloproteinase 7 | SQDDIKGIQKLYGKRS |
| 2 | ADF-002 | Adipophilin | VMAGDIYSV |
| 3 | ADF-001 | Adipophilin | SVASTITGV |
| 4 | APO-001 | Apolipoprotein L1 | ALADGVQKV |
| 5 | CCN-001 | Cyclin D1 | LLGATCMFV |
| 6 | GUC-001 | GUCY1A3 | SVFAGVVGV |
| 7 | K67-001 | KIAA0367 | ALFDGDPHL |

TABLE 4A-continued

IMA901 (e.g. used in renal cancer)

| SEQ ID No: | Abbrev. | Protein | Sequence |
| --- | --- | --- | --- |
| 8 | MET-001 | c met proto oncogene | YVDPVITSI |
| 9 | MUC-001 | MUC1 | STAPPVHNV |
| 10 | RGS-001 | RGS 5 | LAALPHSCL |

TABLE 4B

IMA910 (e.g. used in colon cancer)

| SEQ ID No: | Abbrev. | Sequence |
| --- | --- | --- |
| 11 | C20-001 | ALSNLEVTL |
| 12 | NOX-001 | ILAPVILYI |
| 13 | ODC-001 | ILDQKINEV |
| 14 | PCN-001 | KLMDLDVEQL |
| 15 | TGFBI-001 | ALFVRLLALA |
| 16 | TOP-001 | KIFDEILVNA |
| 17 | TGFBI-004 | TPPIDAHTRNLLRNH |
| 18 | CEA-006 | SPQYSWRINGIPQQHT |
| 5 | CCN-001 | LLGATCMFV |
| 9 | MUC-001 | STAPPVHNV |
| 1 | MMP-001 | SQDDIKGIQKLYGKRS |
| 19 | CEA-004 | YLSGANLNL |
| 8 | MET-001 | YVDPVITSI |

TABLE 4C

IMA941 (e.g. used in gastric cancer)

| SEQ ID NO | Peptide ID | Sequence |
| --- | --- | --- |
| 20 | CDC2-001 | LYQILQGIVF |
| 21 | ASPM-002 | SYNPLWLRI |
| 22 | UCHL5-001 | NYLPFIMEL |
| 23 | MET-006 | SYIDVLPEF |
| 24 | PROM1-001 | SYIIDPLNL |
| 25 | UQCRB-001 | YYNAAGFNKL |
| 26 | MST1R-001 | NYLLYVSNF |
| 27 | PPAP2C-001 | AYLVYTDRL |
| 28 | SMC4-001 | HYKPTPLYF |
| 29 | MMP11-001 | VWSDVTPLTF |

TABLE 4D

IMA950 (e.g. used in glioblastoma)

| SEQ ID NO | Peptide ID | Sequence |
|---|---|---|
| 30 | CSP-001 | TMLARLASA |
| 31 | FABP7-001 | LTFGDVVAV |
| 32 | NLGN4X-001 | NLDTLMTYV |
| 33 | TNC-001 | AMTQLLAGV |
| 34 | NRCAM-001 | GLWHHQTEV |
| 35 | IGF2BP3-001 | KIQEILTQV |
| 36 | BCA-002 | ALWAWPSEL |
| 37 | MET-005 | TFSYVDPVITSISPKYG |

Therefore, in yet another preferred aspect of the method according to the present invention, said anti-cancer vaccine is selected from an anti-cancer vaccine comprising a mixture of immunogenic peptides having a sequence selected from SEQ ID No. 1 to 10; SEQ ID No. 11 to 19 and 1, 5, 8, and 9; SEQ ID No. 20 to 29, and SEQ ID No. 30 to 37. As stated above, said vaccine preferably contains a vaccine, such as GM-CSF, and optionally additional buffers and control peptides (e.g. a viral peptide).

Yet another preferred aspect of the present invention then relates to a diagnostic kit, comprising materials for performing a method according to the present invention as described herein, in one or separate containers, comprising at least one antibody specific for CD15; IL4Ra; CD14; CD11 b; HLA-DR; CD33; Lin, and CD45; and optionally CD18; CD80; CD83; CD86; HLA-DR; HLA-I, optionally together with instructions for performing said method.

The present invention also includes a kit comprising:
(a) a container that contains a composition of immunogenic TAA-peptides and/or antibodies as described above, in solution or in lyophilized form;
(b) optionally a second container containing a diluent or reconstituting solution for the lyophilized formulation(s); and
(c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to certain antibody or peptide concentrations as suitable for diagnosis and the above methods, such as cytometry.

Preferred is a diagnostic kit according to the present invention, wherein the antibody is labeled with a fluorochrome selected from Q605, V450, AF700, APC-H7, PE-Cy7, FITC and Aqua dye (for example LIVE/DEAD® Fixable Aqua Dead Cell Stain Kit from Invitrogen). Even more preferred is a kit comprising at least one antibody that is specific for each of the markers CD15; IL4Ra; CD14; CD11b; HLA-DR; CD33; Lin; and, optionally CD45; CD18; CD80; CD83; CD86; HLA-I and a Live/Dead discriminator.

Most preferred is a kit comprising at least one antibody selected from CD15-V450, CD124-PE, CD11b-AF700, CD14-APC-H7, CD33-PE-Cy7, CD3-FITC, CD19-FITC, CD56-FITC, CD14-FITC, and optionally Live-Dead Aqua dye, and CD45-Q605.

Yet another preferred aspect of the present invention then relates to a method for inducing an immune response in a cancer patient, comprising a) administering an anti-cancer vaccine to said cancer patient, b) performing a method according to the present invention in a biological sample obtained from said patient being treated for cancer, wherein a decrease of the level of said MDSC phenotype(s) as determined compared to a patient sample before the treatment is indicative for the induction of an immune response in a cancer patient, and c) optionally, repeating step a) based on the results as obtained in step b).

According to the inventors' knowledge, for the first time a broad range of myeloid-derived suppressor cell (MDSC) phenotypes can be aniseed systematically in cancer, such as renal cell carcinoma patients. Six different MDSC populations were defined prospectively. All populations were correlated, and 5/6 MDSC populations were highly significantly increased in patients compared to healthy donors. Interestingly, low levels of MDSCs were associated with multiple immune responses after CY treatment. Furthermore, a highly significant inverse correlation of MDSC levels with overall survival was found. Thus MDSCs are a diagnostic, prognostic and predictive marker for RCC and CRC.

Yet another preferred aspect of the present invention then relates to an improved method for treating cancer in a cancer patient in need thereof, comprising administering a suitable anti-cancer treatment to said cancer patient which decreases the level of at least one of said MDSC phenotype(s) as determined through a method according to the present invention in a biological sample obtained from said patient being treated for cancer, compared to a patient sample before said treatment. Said treatment can be a pre-treatment before an immunotherapy (or "first line of treatment"), or an adjuvant therapy, as needed.

Suitable methods for changing the number and/or population of MDSCs, as well as other methods influencing the MDSC pathway are also described in Ugel et al. (Ugel S, Delpozzo F, Desantis G, Papalini F, Simonato F, Sonda N, Zilio S, Bronte V. Therapeutic targeting of myeloid-derived suppressor cells. Curr Opin Pharmacol. 2009 August; 9(4): 470-81. Epub 2009 Jul. 16), and can be employed by the person of skill in the context of the present invention.

The cancer treatment can be selected from any treatment suitable for the respective cancer, and is, for example, selected from chemotherapy with an anti-cancer agent, and/or selected from cytokines, sorafenib, sunitinib, cyclophosphamide, and tyrosine kinase inhibitors (TKI) and/or immunotherapy, preferably comprising the use of an anti-cancer vaccine, for example as described herein, optionally together with GM-CSF.

Yet another preferred aspect of the present invention then relates to an improved method for treating cancer in a cancer patient in need thereof, comprising a) administering an anti-cancer vaccine to said cancer patient, b) performing a method according to the present invention in a biological sample obtained from said patient being treated for cancer, wherein a decrease of the level of said MDSC phenotype(s) as determined compared to a patient sample before the treatment is indicative for a treatment and/or improved treatment of said cancer in said cancer patient, and c) optionally, repeating step a) based on the results as obtained in step b).

In these therapeutic aspects of the present invention, the methods according to the present invention are used in order to provide improved treatment options in the therapy, in particular immunotherapy, of cancers. The methods according to the invention provide additional and early information regarding the need and the effect of an immunological treatment of cancer, and thus allow for more informed decisions regarding the further treatment of said cancer. Thus, preferred is a method according as above, which further comprises a monitoring of the immune response and/or treatment in said cancer patient, comprising repeating step b), and optionally step c) at least once.

The methods according to the present invention also allow a better prognosis regarding the future outcome of the current treatment, wherein an increased level of said MDSC phenotypes compared to pre-treatment MDSC levels in a sample is associated with shorter overall survival, tumor growth or progression-free survival. Again, this allows for more informed decisions regarding the further treatment of said cancer.

As described above, preferred treatments or pre-treatments in addition to the immunotherapeutic vaccines as described above are selected from an anti-cancer agent selected from cytokines, sorafenib, sunitinib, cyclophosphamide, and tyrosine kinase inhibitors (TKI). The cancers to be treated can be all cancers which are responsive to immunotherapy, and are preferably selected from renal cell carcinoma (RCC), colorectal cancer (CRC), gastric cancer (GC), melanoma, and adenocarcinoma.

It should be understood that the features of the invention as disclosed and described herein can be used not only in the respective combination as indicated but also in a singular fashion without departing from the intended scope of the present invention.

The invention will now be described in more detail in the examples with reference to the sequence listing. The following examples are provided for illustrative purposes only and are not intended to limit the invention.

FIG. 1 shows an exemplary MDSC staining with the respective gating strategy. Identical gates were used for all samples. MDSC1-2 and lymphocytes were gated as subpopulations from singlets and living lymphocytes while MDSC3-6 were gated as subpopulations from singlets.

FIGS. 2a) to 2f) show the comparison of IMA901-202 patients and age-matched healthy donors. Shown are pre-treatment MDSC levels of individual patients of the ITT populations that were MDSC evaluable and age <70 years (N=52) and of healthy donors (N=22). Bars denote medians, p-values have been calculated by Mann-Whitney test, 2-sided.

In the sequence listing, SEQ ID No: 1 to SEQ ID No: 37 show TUMAPs as included in preferred vaccines to be used in the context of the present invention.

EXAMPLES

A flow cytometry panel was established that could identify all six MDSC populations by a single multicolor staining. This assay was performed for all available pre-treatment patient samples of the tested IMA901-202 ITT population (N=67 available, N=61 evaluable), matched healthy donor samples (N=22 available, N=22 evaluable).

Comparison of Study Patients with Age-Matched Healthy Donors

For comparison of pre-treatment levels with healthy donors, only intention-to-treat (ITT) patients below the age of 70 were selected to match the oldest healthy control donors. The resulting groups of patients (N=52) and healthy donors (N=22) were balanced with respect to age, gender and CMV seropositivity. It was found that—while levels of MDSC1 were different between patients and healthy donors—levels of MDSC2, 3, 4, 5 and 6 were highly significantly increased in patients as compared to healthy donors.

Correlations Between Baseline Parameters and MDSC Levels

Within the MDSC evaluable ITT population (N=61), it was found that both study arms (+ or −Cy) were balanced with respect to MDSC1-6 levels, thus showed no significant differences. Prior treatment with sorafenib was associated with significantly lower pre-treatment MDSC2 levels (p=0.0278 [Mann-Whitney-Test]; same trend for MDSC1 levels). These data are compatible with the hypothesis that sorafenib may influence myeloid maturation processes. A potentially related prior observation is that sorafenib has been shown to impair human DC maturation in vitro via inhibition of PI3 and MAP kinases and NFκB signaling.

Correlations Between Pre-Treatment MDSC Levels and Immune Responses

The correlation of pre-treatment MDSC levels with immune responses was analyzed in the Per Protocol PP patient population with evaluable pre-treatment MDSC levels and evaluable overall immune responses (N=54). The subgroup analysis was performed with respect to CY pre-treatment (yes/no). No general association of increased immune responses with lower pre-treatment MDSC1-6 levels was found in the total PP patient population. Interestingly, in the CY subgroup only, there was a strong trend that multi-TUMAP responses were associated with lower MDSC5 levels (p=0.0524; two-sided Mann-Whitney-Test).

TABLE 5

Correlation of pre-treatment MDSC levels and overall survival (study arm subgroups)

| | All (N = 57) | | +Cy (N = 26) | | −Cy (N = 31) | |
|---|---|---|---|---|---|---|
| | HR estimate | p | HR estimate | p | HR estimate | p |
| MDSC1 | 6.9617 | 0.6307 | 3743.4765 | 0.1766 | 0.0527 | 0.6061 |
| MDSC2 | 2.0059 | 0.5076 | 1.1694 | 0.9640 | 1.4980 | 0.7150 |
| MDSC3 | 2.0681 | *0.1133* | 2.8586 | 0.1841 | 1.7469 | 0.3629 |
| MDSC4 | 1.0693 | *0.0332* | 1.0885 | *0.0987* | 1.0463 | 0.2539 |
| MDSC5 | 1.0965 | *0.0053* | 1.1499 | *0.0837* | 1.0745 | *0.0499* |
| MDSC6 | 1.0703 | *0.0687* | 0.9703 | 0.7992 | 1.0621 | *0.1057* |

Shown are HR estimates (cox proportional hazard model, estimated hazard ratio) and p values (likelihood ratio test) for analysis of pre-treatment MDSC levels as % per lymphocytes versus overall survival in the per protocol population that is evaluable for MDSC levels. Italic numbers indicate trends (p<0.15). Bold number indicate a Hazard Ratio>1: Time to event shorter for patients with higher values.

Correlations Between Pre-Treatment MDSC Levels and Clinical Responses

When pre-treatment MDSC levels of the total PP patient population were compared to overall survival (N=57 evaluable) several significant correlations (MDSC4, 5) and trends (MDSC3, 6) were found. As hypothesized, increased pre-treatment MDSC levels were always associated with shorter overall survival. Therefore, a clear biomarker role for MDSCs was identified in IMA901-202 that was either prognostic for disease or predictive for response to IMA901 treatment. For several MDSC phenotypes, the trend for differentiation between prognostic vs. predictive markers was more pronounced in patients that developed immune responses to IMA901 and in CY pretreated patients, which indicates a role as predictive biomarker that influence the effectiveness of IMA901-induced T-cell responses, possibly by inhibiting the functionality of T-cell responses induced by (in this case) IMA901.

Assays

An assay was performed with IMA901-202 samples (as prospectively defined) using PBMCs from all available IMA901-202 patients at one pre-treatment time point; age matched healthy donor PBMCs and internal control PBMCs (pre-treatment dataset).

For the assay, cryoconserved PBMCs were thawed and incubated with nucleases to prevent clumping. Cells were first stained with a live/dead discriminator dye. Cells were then blocked with hIgG to reduce subsequent Fc-mediated binding. Cells were then surface stained with fluorochrome labeled antibodies to CD15, CD11b, CD124, CD14, CD33, CD3, CD19, CD56 and CD45. After erythrocyte lysis cells were fixed with formaldehyde. Measurement was performed on a BD LSR II SORP instrument equipped with a blue, violet, red and green laser and optimized dichroic mirrors plus band pass filters for all dyes. Optimized instrument settings were used and automated instrument calibration was performed before each experiment to ensure comparability between assays. Primary data analysis was performed with FlowJo 8.8.6. Identical gates were used for analysis of all samples and among both assays. Samples were set evaluable if at least 75.000 live CD45+ lymphocytes were counted. Statistical analysis of derived data was performed with GraphPad Prism 4 and Statgraphics Centurion XV.

Materials and Methods

Peripheral blood mononuclear cells (PBMCs) were obtained within 8 hours from heparinized blood samples using standard ficoll gradient separation and were cryoconserved before batch analysis.

In order to quantify levels of MDSCs among PBMCs, samples were thawed, washed twice with PBS (Lonza, Cologne, Germany) and stained with the dead cell dye Live/Dead Aqua (Invitrogen, Karlsruhe, Germany) diluted in PBS at 4° C. for 30 minutes. Staining buffer for all further steps was PBEA, which is PBS supplemented with 0.5% BSA (Sigma-Aldrich, Taufkirchen, Germany), 2 mM EDTA (Roth, Karlsruhe. Germany) and 10 mg/ml sodium azide (Merck. Darmstadt, Germany). Cells were further washed. Blocking of Fc receptors was performed by incubation with 0.29 mg/ml hIgG (AbD Serotec, Düsseldorf, Germany) for 15 minutes at room temperature. Cells were then stained with antibodies CD45 Q605 (Invitrogen), CD15 V450, CD124 PE, CD11b AF700, CD14 APC-H7, CD33 PE-Cy7, CD3 FITC, CD19 FITC, CD56 FITC, CD14 FITC (all from BD) at 4° C. for 30 minutes in the presence of 0.29 mg/ml hIgG.

LITERATURE AS CITED

Mandruzzato S, Solito S, Falisi E, Francescato S, Chiarion-Sileni V, Mocellin S, Zanon A, Rossi C R, Nitti D, Bronte V, Zanovello P (2009). IL4Ralpha+ myeloid-derived suppressor cell expansion in cancer patients. J. Immunol. 182, 6562-6568.

Kusmartsev S, Su Z, Heiser A, Dannull J, Eruslanov E, Kubler H, Yancey D, Dahm P, Vieweg J (2008). Reversal of myeloid cell-mediated immunosuppression in patients with metastatic renal cell carcinoma. Clin Cancer Res. 14, 8270-8278.

Mirza N, Fishman M, Fricke I, Dunn M, Neuger A M, Frost T J, Lush R M, Antonia S, Gabrilovich D I (2006). All-trans-retinoic acid improves differentiation of myeloid cells and immune response in cancer patients. Cancer Res 66, 9299-9307.

Filipazzi P, Valenti R, Huber V, Pilla L, Canese P, Zero M, Castelli C, Mariani L, Parmiani G, Rivoltini L (2007). Identification of a new subset of myeloid suppressor cells in peripheral blood of melanoma patients with modulation by a granulocyte-macrophage colony-stimulation factor-based antitumor vaccine. J Clin Oncol 25, 2546-2553.

Schmielau J, Finn O J (2001). Activated granulocytes and granulocyte-derived hydrogen peroxide are the underlying mechanism of suppression of t-cell function in advanced cancer patients. Cancer Res. 61, 4756-4760.

Zea A H, Rodriguez P C, Atkins M B, Hernandez C, Signoretti S, Zabaleta J, McDermott D, Quiceno D, Youmans A, O'Neill A, Mier J, Ochoa A C (2005). Arginase-producing myeloid suppressor cells in renal cell carcinoma patients: a mechanism of tumor evasion. Cancer Res. 65, 3044-3048.

The invention claimed is:
1. A method for treating a patient suffering from metastatic renal cell carcinoma or metastatic adenocarcinoma that has been pretreated with cyclophosphamide, comprising:
   a) obtaining a biological sample comprising peripheral blood mononuclear cells (PBMC) from said patient;
   b) contacting the biological sample with a detectably-labeled antibody specific for CD11b, a detectably-labeled antibody specific for CD14, a detectably-labeled antibody specific for CD15, a detectably-labeled antibody specific for CD80, a detectably-labeled antibody specific for CD83, a detectably-labeled antibody specific for CD86, and a detectably-labeled antibody specific for HLA-DR;
   c) quantitating the level of myeloid-derived suppressor cells having MDSC5 phenotype in the patient relative to the level of myeloid-derived suppressor cells having MDSC5 phenotype in a non-treated patient sample by flow cytometry, wherein said MDSC5 phenotype is based on markers CD11b+, CD14−, CD15+, FSChi, SSCim, CD80−, CD83−, CD86−, and HLA-DR−; and
   d) administering an anti-cancer vaccine to said patient if the level of myeloid-derived suppressor cells having MDSC5 phenotype from step (c) is decreased compared to a non-treated patient sample, wherein said anti-cancer vaccine is selected from an anti-cancer vaccine comprising a mixture of immunogenic peptides having a sequence selected from SEQ ID No. 1 to 10; SEQ ID No. 11 to 19 and 1, 5, 8, and 9; SEQ ID No. 20 to 29, and SEQ ID No. 30 to 37.

2. The method according to claim 1, wherein said method comprises flow cytometry comprising a single multicolor staining step.

3. The method according to claim 1, wherein said biological sample is selected from the group consisting of whole blood, peripheral blood, or fractions thereof, buffy coat, tumor tissue, and bone marrow.

4. The method of claim 1, wherein said patient has been pretreated with cyclophosphamide.

5. The method of claim 1, wherein said anti-cancer vaccine is administered together with GM-CSF.

* * * * *